United States Patent
Zhang et al.

(10) Patent No.: US 8,803,958 B2
(45) Date of Patent: Aug. 12, 2014

(54) GLOBAL CAMERA PATH OPTIMIZATION

(75) Inventors: Hongsheng Zhang, Framingham, MA (US); Benjamin FrantzDale, Boston, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 548 days.

(21) Appl. No.: 12/811,239

(22) PCT Filed: Jan. 4, 2009

(86) PCT No.: PCT/US2009/030068
§ 371 (c)(1),
(2), (4) Date: Sep. 22, 2010

(87) PCT Pub. No.: WO2009/089129
PCT Pub. Date: Jul. 16, 2009

(65) Prior Publication Data
US 2011/0007138 A1    Jan. 13, 2011

Related U.S. Application Data

(60) Provisional application No. 61/019,159, filed on Jan. 4, 2008.

(51) Int. Cl.
*H04N 13/02* (2006.01)
*G06K 9/00* (2006.01)
*A61C 13/00* (2006.01)
*G06T 17/00* (2006.01)

(52) U.S. Cl.
CPC ............ *G06T 17/00* (2013.01); *G06K 9/00214* (2013.01); *G06T 2207/10012* (2013.01); *A61C 13/0004* (2013.01); *G06T 2210/41* (2013.01); *H04N 13/0221* (2013.01); *G06K 9/00201* (2013.01)
USPC ............... 348/66; 345/419; 348/335; 348/42; 348/50; 348/51; 382/154; 382/285; 433/24; 433/29

(58) Field of Classification Search
CPC . A61B 19/50; A61B 2019/5251; G06T 19/00
USPC ................ 348/50; 433/29, 215; 382/154, 285
IPC ..................................................... H04N 13/02
See application file for complete search history.

(56) References Cited

U.S. PATENT DOCUMENTS 6,208,347 B1   3/2001  Migdal et al.
6,219,437 B1   4/2001  Baldur
(Continued)

FOREIGN PATENT DOCUMENTS

KR   2007-0039641   4/2007

OTHER PUBLICATIONS

Triggs, Bill, et al. "Bundle adjustment—a modern synthesis." Vision algorithms: theory and practice (2000): 153-177.).*

(Continued)

*Primary Examiner* — Jay Patel
*Assistant Examiner* — Neil Mikeska

(57) ABSTRACT

Disclosed herein are various techniques for improving global path optimization in a system that uses camera path for three-dimensional reconstruction. A subset of frames of data for the global path, the key frames, may be used to reduce the computational complexity of the optimization, while preserving full three-dimensional detail in the optimized model by relating other measurements to the optimized key frame path.

21 Claims, 8 Drawing Sheets

(56) References Cited

U.S. PATENT DOCUMENTS

| | | |
|---|---|---|
| 6,973,204 B2 | 12/2005 | Adachi |
| 7,085,323 B2 | 8/2006 | Hong |
| 7,372,642 B2 | 5/2008 | Rohaly et al. |
| 7,502,505 B2 | 3/2009 | Malvar |
| 7,508,430 B1 | 3/2009 | Oten et al. |
| 7,605,817 B2 | 10/2009 | Zhang et al. |
| 8,073,190 B2 | 12/2011 | Gloudemans |
| 8,228,994 B2 | 7/2012 | Wu |
| 2001/0016063 A1* | 8/2001 | Albeck et al. ............... 382/154 |
| 2001/0033326 A1 | 10/2001 | Goldstein et al. |
| 2002/0136444 A1* | 9/2002 | Brown et al. ............... 382/154 |
| 2004/0051783 A1 | 3/2004 | Chellappa et al. |
| 2004/0197728 A1 | 10/2004 | Abolfathi et al. |
| 2005/0089213 A1 | 4/2005 | Geng |
| 2005/0089214 A1 | 4/2005 | Rubbert et al. |
| 2005/0089822 A1 | 4/2005 | Geng |
| 2005/0182295 A1 | 8/2005 | Soper et al. |
| 2005/0285874 A1 | 12/2005 | Zitnick, II et al. |
| 2006/0066612 A1 | 3/2006 | Yang |
| 2006/0154198 A1* | 7/2006 | Durbin et al. ............... 433/29 |
| 2006/0204076 A1 | 9/2006 | Avanish et al. |
| 2006/0208927 A1 | 9/2006 | Poor et al. |
| 2007/0031064 A1* | 2/2007 | Zhao et al. ............... 382/285 |
| 2007/0103460 A1 | 5/2007 | Zhang et al. |
| 2007/0127813 A1 | 6/2007 | Shah |
| 2007/0141534 A1 | 6/2007 | Wen |
| 2007/0172101 A1 | 7/2007 | Kriveshko et al. |
| 2007/0172112 A1* | 7/2007 | Paley et al. ............... 382/154 |
| 2007/0253618 A1 | 11/2007 | Kim et al. |
| 2008/0025646 A1 | 1/2008 | Aguera y Arcas et al. |
| 2008/0238916 A1 | 10/2008 | Ghosh et al. |
| 2010/0111444 A1* | 5/2010 | Coffman ............... 382/285 |

OTHER PUBLICATIONS

Dorst, "First Order Propagation of the Procrustes Method for 3D Attitude Estimation", IEEE Transactions on Pattern Analysis and Machine Intelligence, vol. 27, No. 2, Feb. 2005, pp. 221-229.

Zhang, "Hierarchical Block-Based Disparity Estimation Using Mean Absolute Difference and Dynamic Programming", Proc. of the Int. Workshop on Very Low Bitrate Video Coding, pp. 114, 118, Athens Greece, Oct. 11-12, 2001.

Kriveshko et al., U.S. Appl. No. 12/811,268, filed Jun. 30, 2010.

Rohaly et al., U.S. Appl. No. 12/811,236, filed Sep. 22, 2010.

Rohaly et al., U.S. Appl. No. 12/811,237, filed Sep. 27, 2010.

Zang et al., U.S. Appl. No. 12/811,242, filed Jun. 30, 2010.

* cited by examiner

GLOBAL CAMERA PATH OPTIMIZATION

CROSS REFERENCE TO RELATED APPLICATIONS

This application is a national stage filing under 35 U.S.C. 371 of PCT/US2009/030068, filed Jan. 4, 2009, which claims priority to U.S. Provisional Application No. 61/019,159, filed Jan. 4, 2008, the disclosure of which is incorporated by reference in its/their entirety herein.

FIELD OF INVENTION

This invention relates generally to three-dimensional imaging and more specifically to optimizing the calculation of a global camera path used in a three-dimensional reconstruction.

BACKGROUND

In one technique for three-dimensional image reconstruction, a number of images or image sets of an object are captured with a camera that travels in a path over the surface of the object. Information from this catalogue of information can then be used to reconstruct a three-dimensional model of the object based upon the camera path and individual three-dimensional measurements captured along the camera path. The path of a camera may be very long and complex involving motion estimation from image to image that accumulates significant errors along its length. These errors can result in a variety of reconstruction artifacts in a resulting three-dimensional model such as double surfaces where the camera path scans the same region twice with an error in camera position between the two scans. Error may also be introduced due to calibration problems, inaccuracies in camera distortion models used to determine three-dimensional data, and so forth.

While various techniques exist for minimizing errors along an entire camera path, there remains a need for improved global path optimization techniques suitable for use with data-intensive path optimizations typical of high-accuracy, three-dimensional reconstruction.

SUMMARY

Disclosed herein are various techniques for improving global path optimization in a system that uses camera path for three-dimensional reconstruction. A subset of frames of data for the global path, the key frames, may be used to reduce the computational complexity of the optimization, while preserving full three-dimensional detail in the optimized model by relating other measurements to the optimized key frame path.

In one aspect, a method of three-dimensional reconstruction that is disclosed herein includes acquiring a plurality of frames of image data of a surface of an object, captured from a camera position along a camera path and including a conventional image of the object from the camera position and data for a three-dimensional reconstruction of the surface of the object; selecting a subset of the frames of image data to provide a plurality of key frames, each one related to at least one other key frame by a portion of the camera path including a rotation and a translation determined based upon one or more common points in the three-dimensional reconstruction, wherein the remaining plurality of frames of image data are non-key frames; providing a three-dimensional model of the object; determining a second rotation and a second translation from one of the key frames to a non-key frame sequentially positioned between the one of the key frames and a sequentially adjacent key frame; obtaining three-dimensional reconstruction information of the surface of the object from the camera position at least one of the non-key frames to provide upsampled three-dimensional data; and adding the upsampled three-dimensional data to the three-dimensional model based upon the second rotation and the second translation. A camera motion may be estimated between two adjacent key frames based on the rotation and the translation. There may be optimizing the estimation of the camera motion between the two adjacent key frames by creating consistency among motion parameters using an overdetermined system of motion constraint equations, wherein the motion parameters are comprised of information on the rotation and the translation. There may also be optimizing the camera motion between two adjacent non-key frames by creating consistency among motion parameters using an overdetermined system of motion constraint equations. The three-dimensional reconstruction may be updated based on the created consistency among the motion parameters. The data for a three-dimensional reconstruction of the surface of the object may be obtained from at least one other channel image to provide disparity data. The three-dimensional model may further comprise generating a three-dimensional model of the object using the camera path and the three-dimensional reconstruction for each of the key frames. Three-dimensional reconstruction information may be obtained of the surface of the object from the camera position for all of the non-key frames between two adjacent key frames. A subset of the plurality of frames may be selected based on a quality metric of the three-dimensional reconstruction. Selecting of the subset of the plurality of frames may be determined using graph analysis to ensure that all of the key frames are utilized in the three-dimensional reconstruction.

In one aspect, a computer program product that is disclosed herein performs the steps of acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; selecting a subset of the plurality of frames of image data to provide a plurality of key frames, each one of the plurality of key frames related to at least one other one of the plurality of key frames by a portion of the camera path including a rotation and a translation determined based upon one or more common points in the three-dimensional reconstruction of the surface of the object in each of the respective key frames, wherein the remaining ones of the plurality of frames of image data are non-key frames; providing a three-dimensional model of the object; determining a second rotation and a second translation from one of the key frames to at least one of the non-key frames sequentially positioned between the one of the key frames and a sequentially adjacent one of the key frames; obtaining three-dimensional reconstruction information of the surface of the object from the camera position of the at least one of the non-key frames to provide upsampled three-dimensional data; and adding the upsampled three-dimensional data to the three-dimensional model based upon the second rotation and the second translation.

In one aspect, a method for interactively reducing accumulated error in a global path is disclosed herein which includes acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; generating a three-dimensional model of the object using the camera path and the data for the three-dimensional reconstruction; identifying two of the plurality of frames of image data that represent a candidate for an accumulated error in the camera path relative to one another; and displaying the three-dimensional model along with a graphical annotation that illustrates a recommended scan path to reduce the accumulated error. The data for a three-dimensional reconstruction of the surface of the object may be obtained from at least one other channel image to provide disparity data. Acquiring one or more frames of image data along the recommended scan path may be accomplished to reduce the accumulated error. Two of the plurality of frames may be identified which further comprises identifying frames of image data that are separated by a substantially greater distance along the camera path than along the surface of the object.

In one aspect, a computer program product comprising computer executable code embodied in a computer readable medium is disclosed herein which performs the steps of acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; generating a three-dimensional model of the object using the camera path and the data for the three-dimensional reconstruction; identifying two of the plurality of frames of image data that represent a candidate for an accumulated error in the camera path relative to one another; and displaying the three-dimensional model along with a graphical annotation that illustrates a recommended scan path to reduce the accumulated error.

In one aspect, a system is disclosed herein which comprises a camera, a monitor, a processor, and a memory, the memory storing a computer program executable by the processor to perform the steps of acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; generating a three-dimensional model of the object using the camera path and the data for the three-dimensional reconstruction; identifying two of the plurality of frames of image data that represent a candidate for an accumulated error in the camera path relative to one another; and displaying the three-dimensional model along with a graphical annotation that illustrates a recommended scan path to reduce the accumulated error.

In one aspect, a method for global path optimization is disclosed herein includes acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; and minimizing an error function for a plurality of camera positions along the camera path, the error function including a system of equations for translational components of an error and for rotational components of the error, wherein the error function couples the translational components and the rotational components using a weighting matrix, thereby providing an optimized camera path. The data for a three-dimensional reconstruction of the surface of the object may be obtained from at least one other channel image to provide disparity data. The system of equations may be a non-linear system of equations. The translational component of the error may form of a system of linear equations. The rotational component of the error may form a system of non-linear equations. A three-dimensional model may be generated based upon the camera path and the data for the three-dimensional reconstruction, and the three-dimensional model may be refined based upon the optimized camera path. A subset of the plurality of frames of image data may be selected to provide a plurality of key frames, each one of the plurality of key frames related to at least one other one of the plurality of key frames by a portion of the camera path including a rotation and a translation determined based upon one or more common points in the three-dimensional reconstruction of the surface of the object in each of the respective key frames, wherein the remaining ones of the plurality of frames of image data are non-key frames. The weighting matrix may be selected to locally decouple the error function around a centroid of common surface data for two or more three-dimensional reconstructions. An error function may be minimized to evaluate a calibration state based on the resulting error function minimization.

In one aspect, a computer program product comprising computer executable code is disclosed herein performs the steps of acquiring a plurality of frames of image data of a surface of an object, each one of the plurality of frames of image data captured from a camera position along a camera path and each one of the plurality of frames of image data including a conventional image of the object from the camera position and data for a three-dimensional reconstruction of the surface of the object as viewed from the camera position; and minimizing an error function for a plurality of camera positions along the camera path, the error function including a system of equations for translational components of an error and for rotational components of the error, wherein the error function couples the translational components and the rotational components using a weighting matrix, thereby providing an optimized camera path.

BRIEF DESCRIPTION OF THE DRAWINGS

The invention and the following detailed description of certain embodiments thereof may be understood by reference to the following figures.

DETAILED DESCRIPTION

Figure 1:
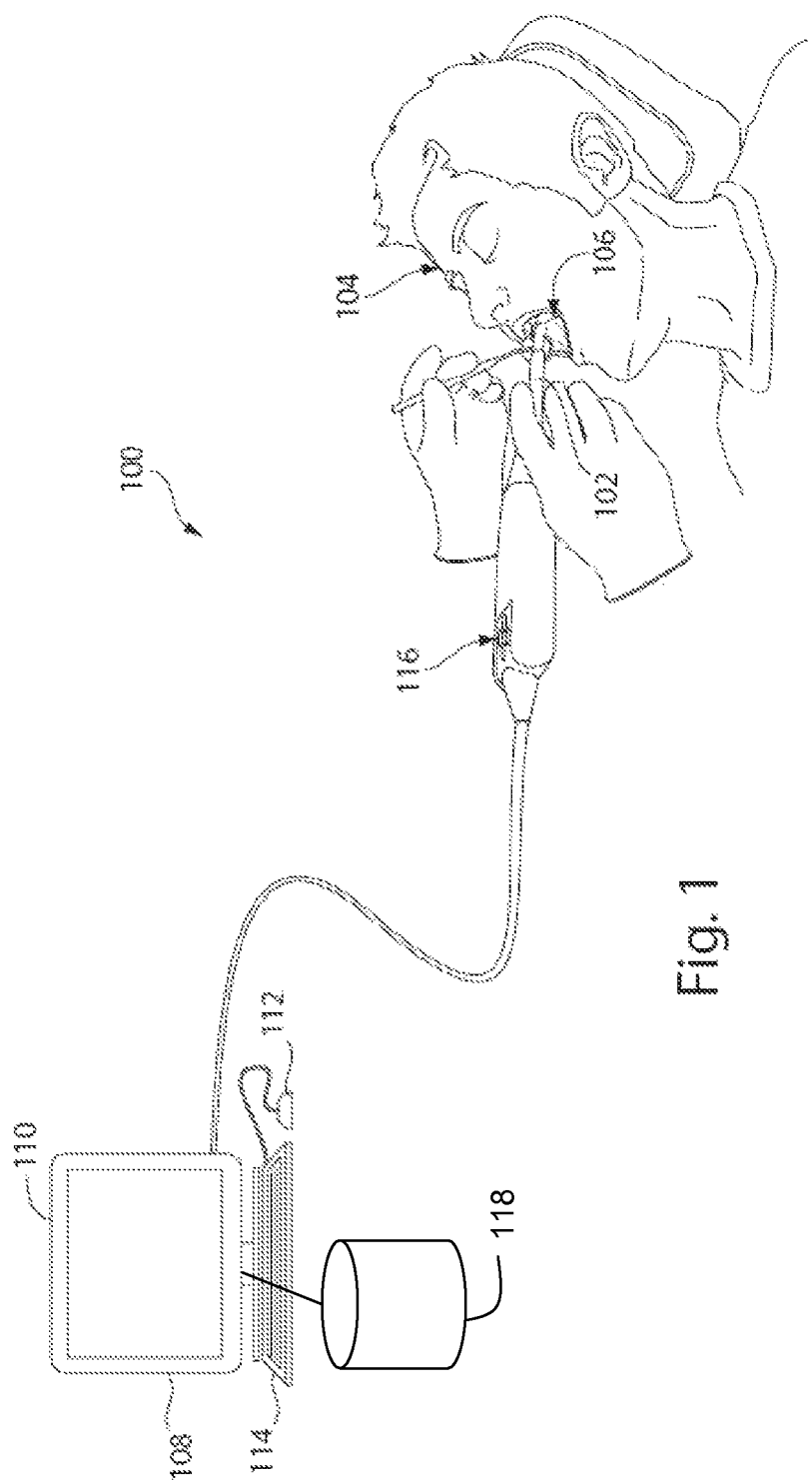
FIG. 1 shows a three-dimensional scanning system.

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

In the systems and methods described herein, a number of techniques for global motion optimization are employed to improve accuracy of three-dimensional reconstructions based upon camera path.

The following description details specific scanning technologies and focuses on dental applications of three-dimensional imaging; however, it will be appreciated that variations, adaptations, and combinations of the methods and systems below will be apparent to one of ordinary skill in the art. For example, while an image-based system is described, non-image based scanning techniques such as infrared time-of-flight techniques or structured light techniques using patterned projections may similarly employ reconstruction based on camera path that may benefit from the improvements described herein. As another example, while digital dentistry is one useful application of the improved accuracy that results from the techniques described herein, global path optimization may also usefully be employed to refine three-dimensional animation models or three-dimensional scans for machine vision applications or for mapping applications. All such variations, adaptations, and combinations are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the system and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, keyboard, display, keypad, track ball, and/or any other device that receives physical input from a user and converts the physical input into an input for use in a computerized system. Thus in the following description the terms "tool", "control" and the like should be broadly construed unless a more specific meaning is otherwise provided or clear from the context.

FIG. 1 depicts a three-dimensional scanning system that may be used with the systems and methods described herein. In general, the system 100 may include a camera 102 that captures images from a surface 106 of an object 104, such as a dental patient, and forwards the images to a computer 108, which may include a display 110 and one or more user-input devices 112, 114 such as a mouse 112 or a keyboard 114. The camera 102 may also include an integrated input or output device 116 such as a control input (e.g., button, touchpad, thumbwheel, etc.) or a display (e.g., LCD or LED display) to provide status information.

The camera 102 may include any camera or camera system suitable for capturing images from which a three-dimensional point cloud or other three-dimensional data may be recovered. For example, the camera 102 may employ a multi-aperture system as disclosed in U.S. Pat. No. 7,372,642 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the camera 102 may include a plurality of apertures including a center aperture positioned along a center optical axis of a lens that provides a center channel for the camera 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, i.e., a video of an object corresponding temporally to a three-dimensional scan of the object, preferably from the same perspective, or from a perspective having a fixed, known relationship to the perspective of the camera 102. The camera 102 may also, or instead, include a stereoscopic, triscopic or other multi-camera or other configuration in which a number of cameras or optical paths are maintained in fixed relation to one another to obtain two-dimensional images of an object from a number of different perspectives. The camera 102 may include suitable processing for deriving a three-dimensional point cloud from an image set or a number of image sets, or each two-dimensional image set may be transmitted to an external processor such as contained in the computer 108 described below. In other embodiments, the camera 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the camera 102 is a handheld, freely-positionable probe having at least one user-input device 116, such as a button, a lever, a dial, a thumbwheel, a switch, or the like, for user control of the image capture system 100 such as starting and stopping scans. In an embodiment, the camera 102 may be shaped and sized for dental scanning. More particularly, the camera 102 may be shaped and sized for intraoral scanning and data capture, such as by insertion into a mouth of an imaging subject and passing over an intraoral surface 106 at a suitable distance to acquire surface data from teeth, gums, and so forth. The camera 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthesis, to ensure proper fitting using a previous scan of corresponding dentition, such as a tooth surface prepared for the prosthesis.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The camera 102 may also, or instead, include a strobe, a flash, or some other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the camera 102 or a separate video system may capture video of the dentition from the point of view of the camera 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, a wax-up, an impression, or a negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may be further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display or the like capable of displaying stereo images.

Communications between the computer 108 and the camera 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the camera 102 to the computer 108 may be secured. The computer 108 may generate control signals to the camera 102 which, in addition to image acquisition commands, may include conventional camera controls such as focus or zoom.

In an example of general operation of a three-dimensional image capture system 100, the camera 102 may acquire two-dimensional image sets at a video rate while the camera 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the camera 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the various processes described herein. The computer-usable medium 118 may also, or instead, store data received from the camera 102, store a three-dimensional model of the object 104, store computer code for rendering and display, and so forth.

Figure 2:
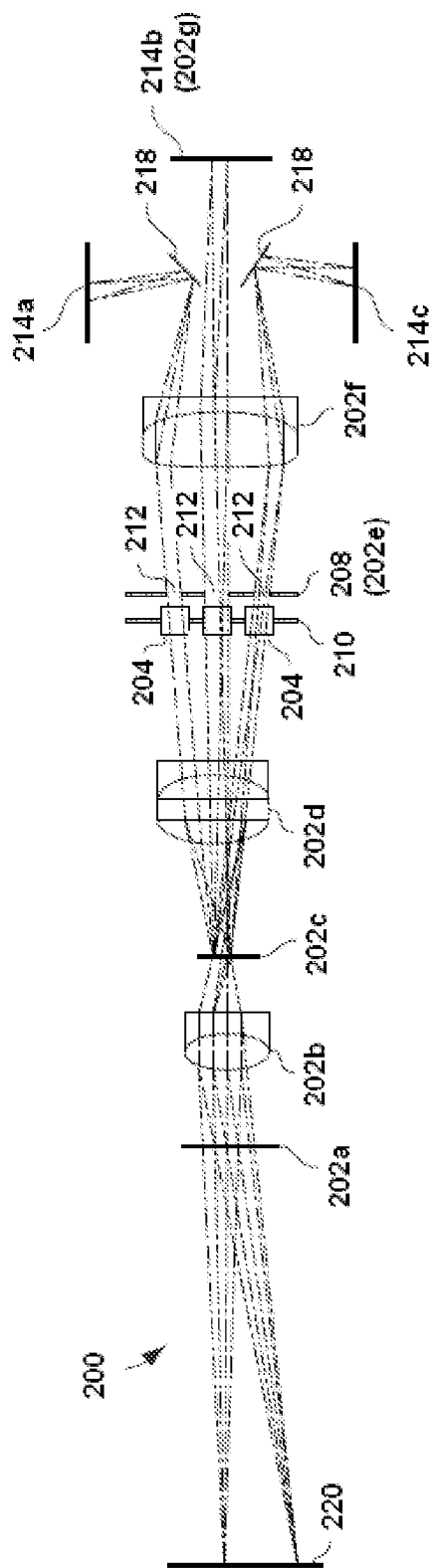
FIG. 2 shows a schematic diagram of an optical system for a three-dimensional camera.

FIG. 2 depicts an optical system 200 for a three-dimensional camera that may be used with the systems and methods described herein, such as for the camera 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202b, a field lens 202d, a relay lens 202f, and so forth. The object lens 202b may be located at or near an entrance pupil 202a of the optical system 200. The field lens 202d may be located at or near a first image plane 202c of the optical system 200. The relay lens 202f may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214a, 214b, 214c.

The optical system 200 may be designed for active wavefront sampling, which should be understood to encompass any technique used to sample a series or collection of optical data from an object 220 or objects, including optical data used to help detect two-dimensional or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642, the entire content of which is incorporated herein by reference. More generally, it will be understood that, while FIG. 2 depicts one embodiment of an optical system 200, numerous variations are possible. One salient feature of the optical system related to the discussion below is the use of a center optical channel that captures conventional video or still images at one of the sensors 214b concurrent with various offset data (at, e.g., 214a and 214c) used to capture three-dimensional measurements. This center channel image may be presented in a user interface to permit inspection, marking, and other manipulation by a user during a user session as describe below.

Figure 3:
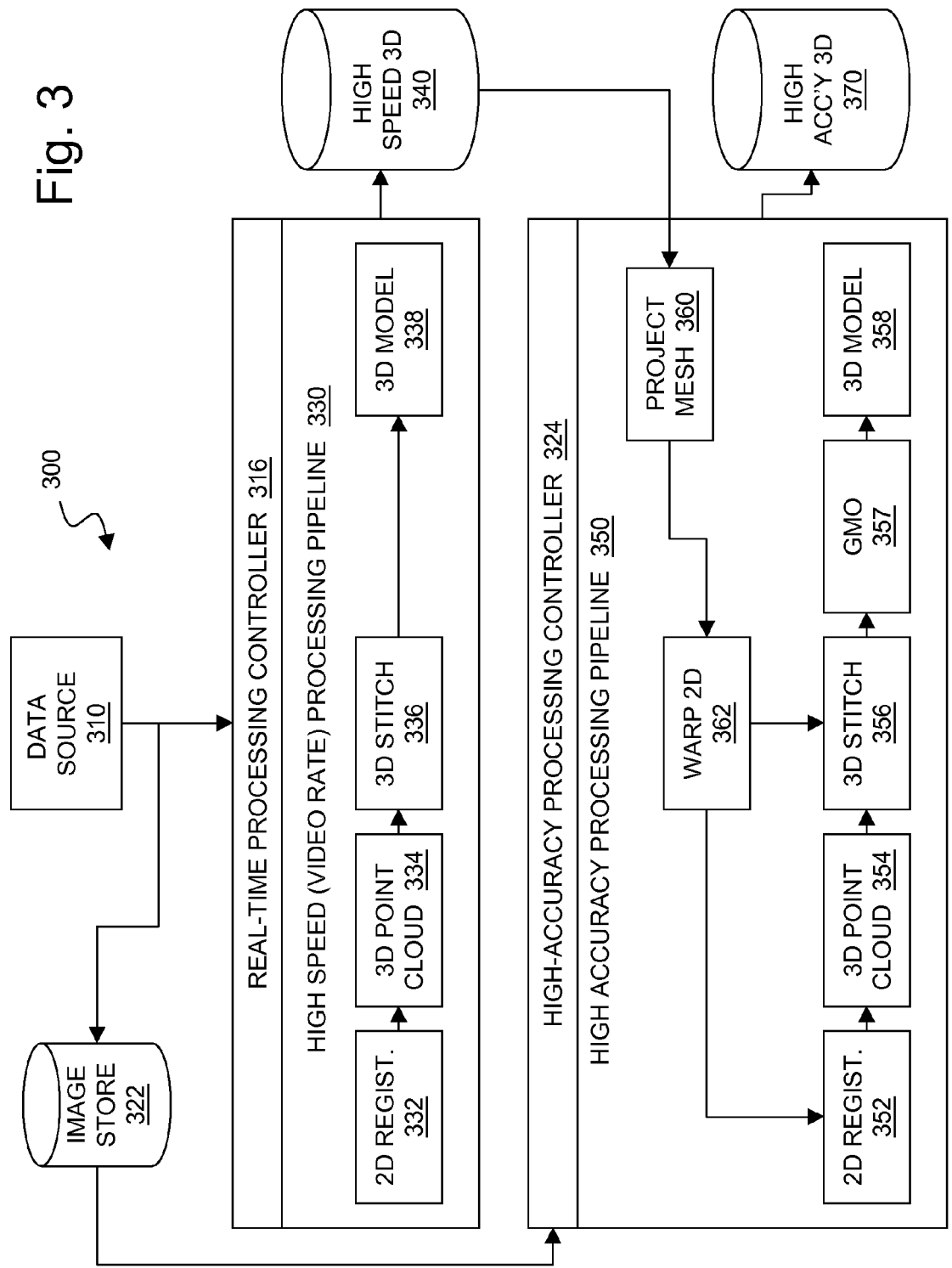
FIG. 3 shows a processing pipeline for obtaining three-dimensional data from a video camera.

FIG. 3 shows a three-dimensional reconstruction system 300 employing a high-speed pipeline and a high-accuracy pipeline. In general, the high-speed processing pipeline 330 aims to provide three-dimensional data in real time, such as at a video frame rate used by an associated display, while the high-accuracy processing pipeline 350 aims to provide the highest accuracy possible from camera measurements, subject to any external computation or time constraints imposed by system hardware or an intended use of the results. A data source 310 such as the camera 102 described above provides image data or the like to the system 300. The data source 310 may for example include hardware such as LED ring lights, wand sensors, a frame grabber, a computer, an operating system and any other suitable hardware and/or software for obtaining data used in a three-dimensional reconstruction. Images from the data source 310, such as center channel images containing conventional video images and side channels containing disparity data used to recover depth information may be passed to the real-time processing controller 316. The real-time processing controller 316 may also provide camera control information or other feedback to the data source 310 to be used in subsequent data acquisition or for specifying data already obtained in the data source 310 that is needed by the real-time processing controller 316. Full resolution images and related image data may be retained in a full resolution image store 322. The stored images may, for example, be provided to the high-accuracy processing controller 324 during processing, or be retained for image review by a human user during subsequent processing steps.

The real-time processing controller 316 may provide images or frames to the high-speed (video rate) processing pipeline 330 for reconstruction of three-dimensional surfaces from the two-dimensional source data in real time. In an exemplary embodiment, two-dimensional images from an image set such as side channel images, may be registered by a two-dimensional image registration module 332. Based on the results of the two-dimensional image registration, a three-dimensional point cloud generation module 334 may create a three-dimensional point cloud or other three-dimensional representation. The three-dimensional point clouds from individual image sets may be combined by a three-dimensional stitching module 336. Finally, the stitched measurements may be combined into an integrated three-dimensional model by a three-dimensional model creation module 338. The resulting model may be stored as a high-speed three-dimensional model 340.

The high-accuracy processing controller 324 may provide images or frames to the high-accuracy processing pipeline 350. Separate image sets may have two-dimensional image registration performed by a two-dimensional image registration module 352. Based on the results of the two-dimensional image registration a three-dimensional point cloud or other three-dimensional representation may be generated by a three-dimensional point cloud generation module 354. The three-dimensional point clouds from individual image sets may be connected using a three-dimensional stitching module 356. Global motion optimization, also referred to herein as global path optimization or global camera path optimization, may be performed by a global motion optimization module 357 in order to reduce errors in the resulting three-dimensional model 358. In general, the path of the camera as it obtains the image frames may be calculated as a part of the three-dimensional reconstruction process. In a post-processing refinement procedure, the calculation of camera path may be optimized—that is, the accumulation of errors along the length of the camera path may be minimized by supplemental frame-to-frame motion estimation with some or all of the global path information. Based on global information such as individual frames of data in the image store 322, the high-speed three-dimensional model 340, and intermediate results in the high-accuracy processing pipeline 350, the high-accuracy model 370 may be processed to reduce errors in the camera path and resulting artifacts in the reconstructed model. As a further refinement, a mesh may be projected onto the high-speed model by a mesh projection module 360. The resulting images may be warped or deformed by a warping module 362. Warped images may be used to ease alignment and stitching between images, such as by reducing the initial error in a motion estimate. The warped images may be provided to the two-dimensional image registration module 352. The feedback of the high-accuracy three-dimensional model 370 into the pipeline may be repeated until some metric is obtained, such as a stitching accuracy or a minimum error threshold.

Various aspects of the system 300 of FIG. 3 are described in greater detail below. In particular, a model refinement process is described that may be used by the high-accuracy processing controller 324 to refine the high accuracy three-dimensional model 370 using measured data in the image store 322. It should be understood that various processing modules, or the steps implied by the modules, shown in this figure are exemplary in nature and that the order of processing, or the steps of the processing sequence, may be modified, omitted, repeated, re-ordered, or supplemented, without departing from the scope of this disclosure.

Figure 4A:
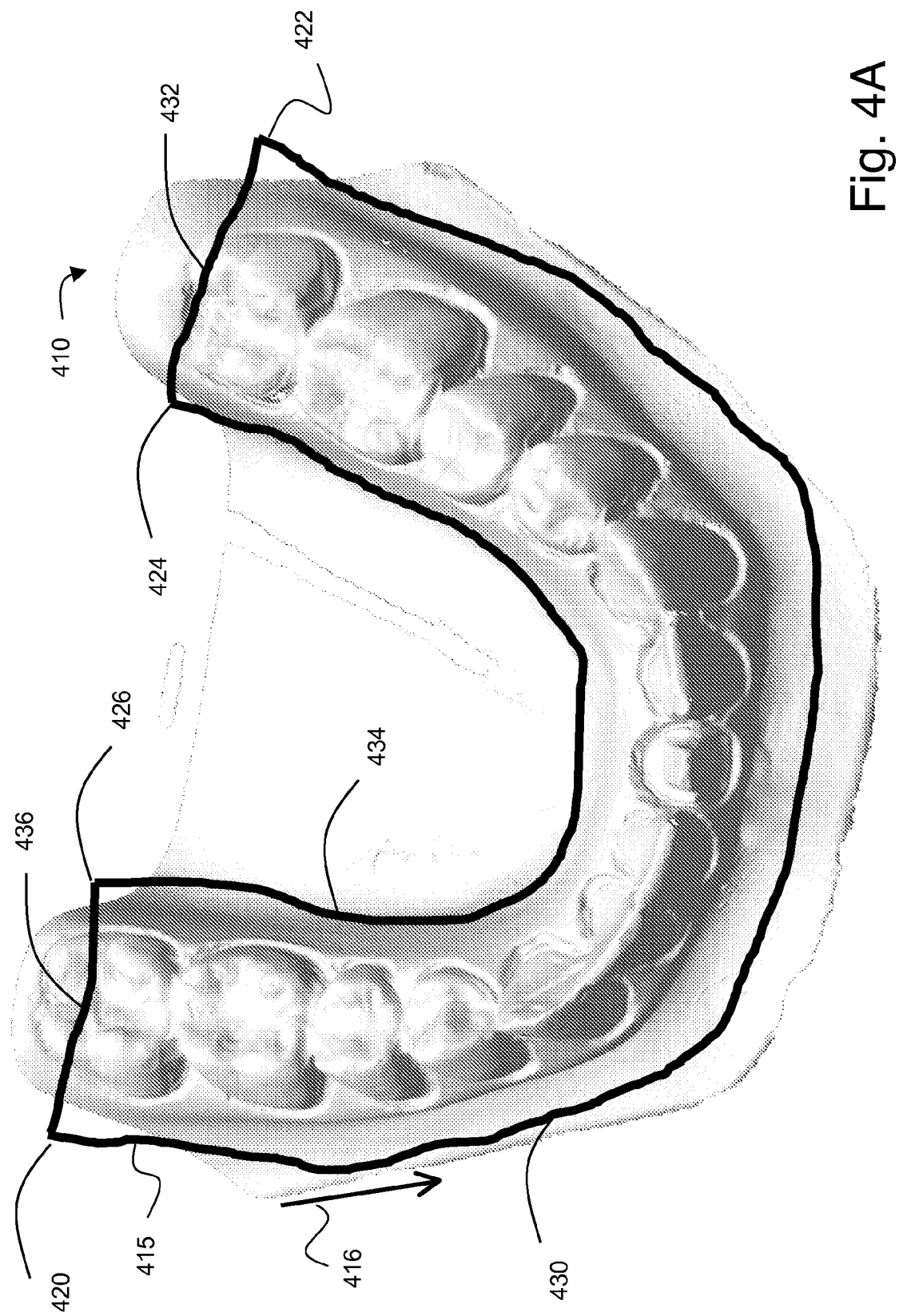
FIGS. 4A and 4B illustrate camera paths for a three-dimensional camera.

FIG. 4A shows an object 410 for imaging, along with a path 415 that a camera may follow while obtaining a three-dimensional scan of a surface of the object 410. The direction of the path 415 is indicated generally by an arrow 416. The object 410 may be an upper dental impression (as shown) or any other object from which three-dimensional surface data is sought. Starting the camera at a starting point 420, the camera may follow an arc 430 to a second point 422. The camera may then follow a segment 432 to a third point 424. The camera may then follow a second arc 434 to a fourth point 426. The camera may then follow a second segment 436 to return approximately to the starting point 420. It should be noted that the path 415 followed by the camera may be irregular rather than smooth, and that while a particular path 415 is depicted, more generally any path may be taken by the camera including paths that double back upon themselves, cross over identical regions two or more times, and/or entirely skip various surfaces of the object 410. It should also be noted that the camera path 415 may usefully return to the starting point 420, but this is not strictly required for three-dimensional reconstruction as described herein. The camera may take hundreds or thousands of images or more as the camera traverses the path around such a dental object 410.

Figure 4B:
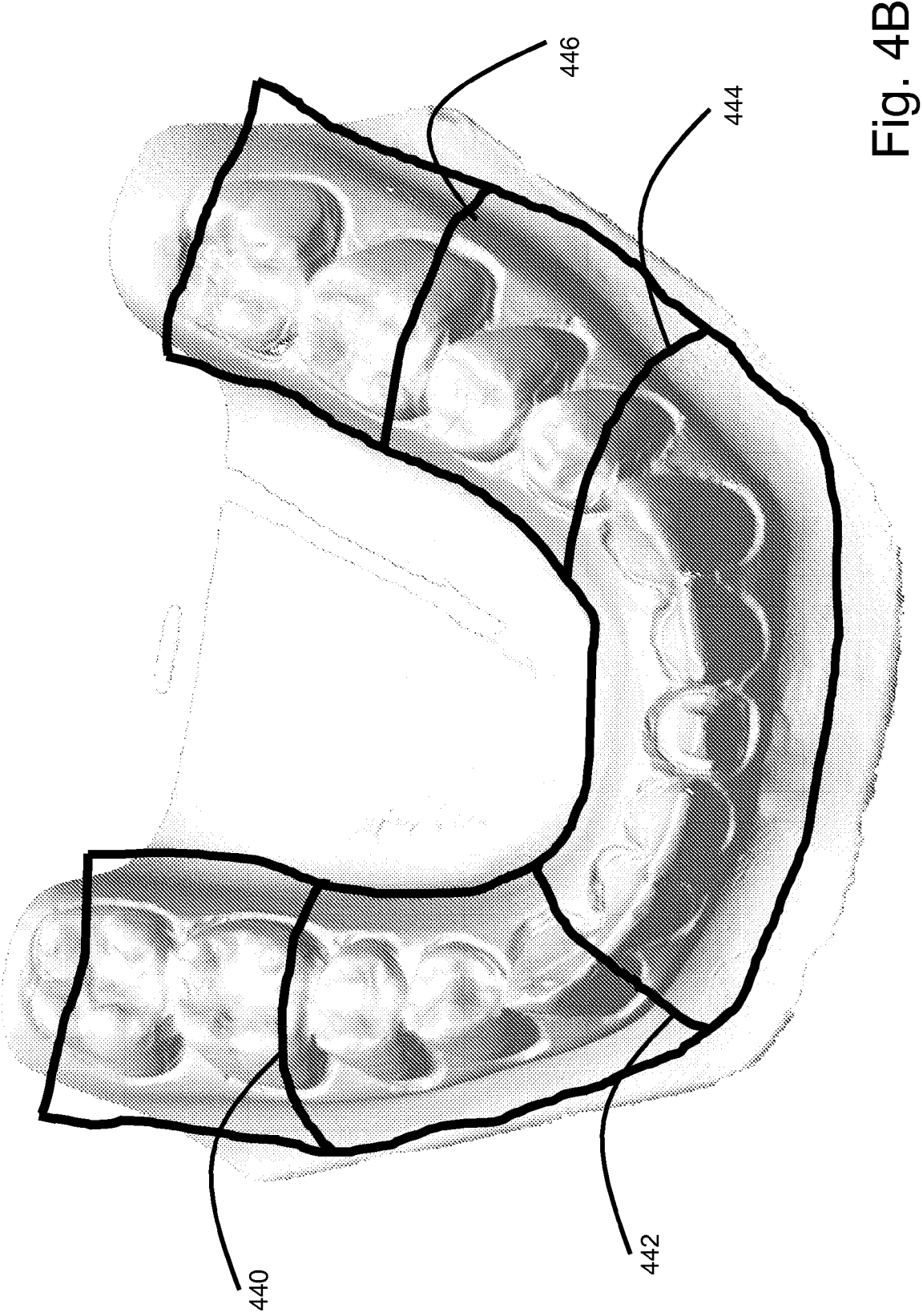

FIG. 4B shows locations where additional scan data might usefully be acquired to improve the accuracy of a three-dimensional reconstruction. For example, arcs 440, 442, 444, and 446 may be scanned (e.g., traversed by the camera path) to provide cross linking between various lengths of the camera path. Data might usefully be acquired, for example, from any area that can improve computational accuracy of a three-dimensional reconstruction such as regions where the length of a camera path between two measurements of the surface (e.g., image sets or image data) is significantly greater than the distance between the two corresponding surface locations in the world coordinate system for the camera path. As another example, this may include regions where separate three-dimensional measurements for a general region of the reconstructed three-dimensional model fail to register to one another, or more generally where portions of the model or individual measurements contain indicia of accumulated error in the global camera path. Key frames (as described below) may be used to focus this inquiry on a subset of measurements that provide coverage for all or a substantial portion of the scanned subject matter.

Figure 5:
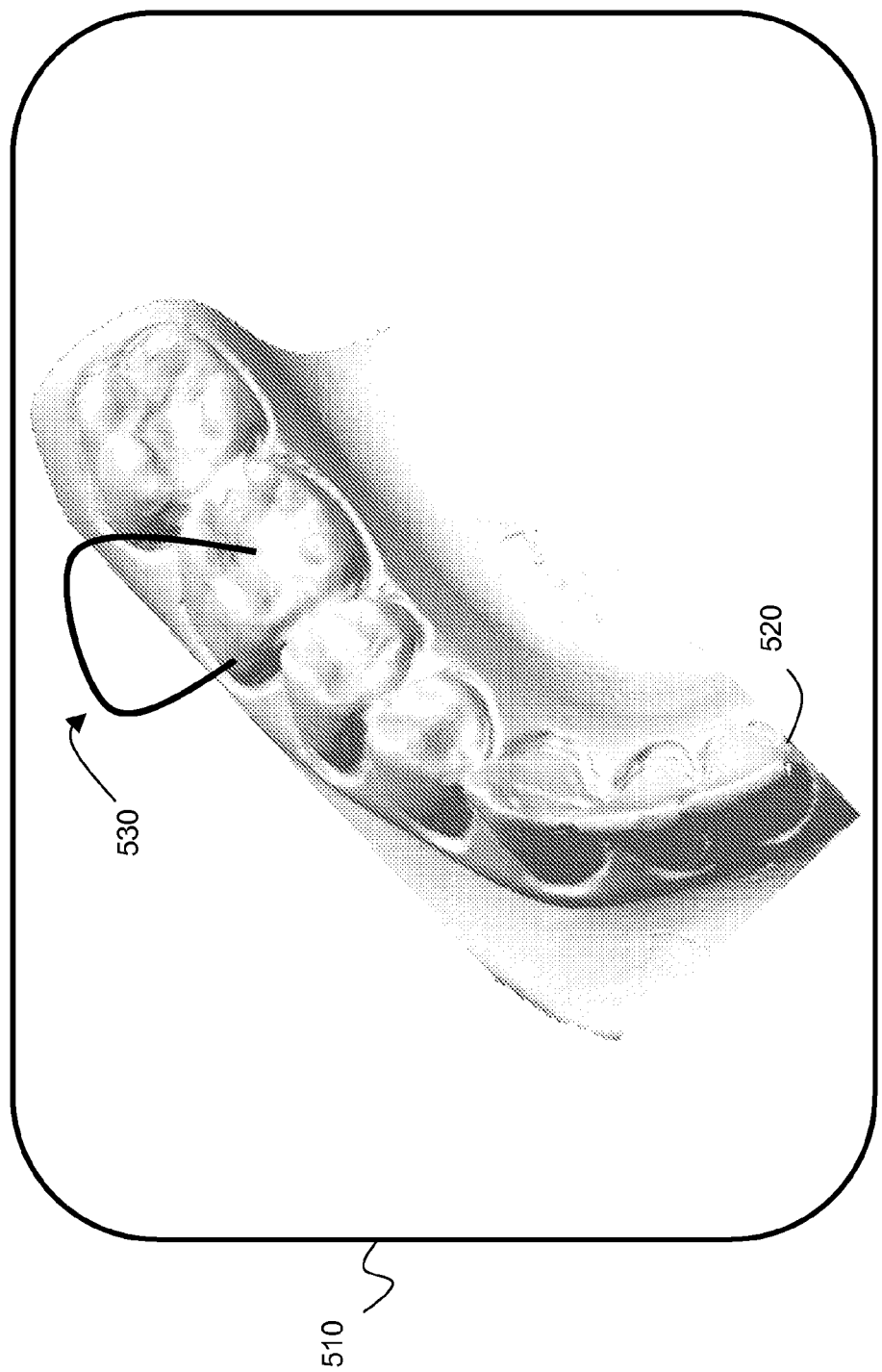
FIG. 5 shows a user interface image where additional data is requested by a software tool.

FIG. 5 shows a user interface depicting a graphical request for additional scan data. After the camera follows the path 415 illustrated above, a software tool may be used to identify various locations where additional data might usefully be acquired to reduce accumulated error in a global camera path, as discussed above. A monitor 510 may display an image 520 such as a three-dimensional reconstruction of scanned subject matter, and an arrow 530 may be displayed on the monitor 510 indicating where additional scanning is recommended. The user may then proceed to use a camera, such as the camera 102 from FIG. 1, to scan the area indicated by the arrow 530. More generally, areas for additional scanning may be identified to a user in a graphical user interface that displays a reconstructed three-dimensional model from the camera path, along with arrows or other identifiers or graphical annotations that illustrate a recommended scan path. After a user augments a camera path with additional scans, the resulting data can be employed to resolve differences (i.e., errors) in the global camera path, as described generally throughout this disclosure.

Figure 6B:
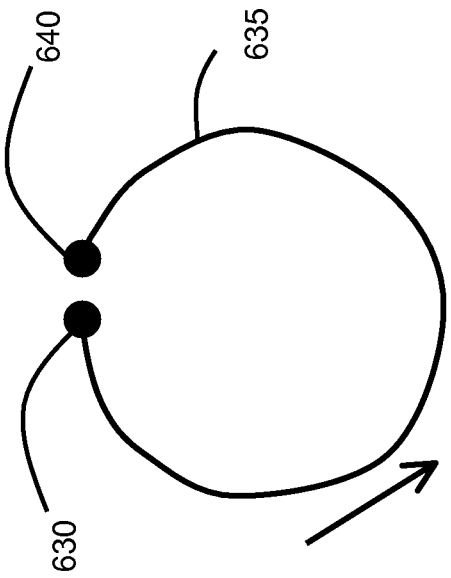
FIGS. 6A and 6B illustrate accumulated error in camera paths.
Figure 6A:
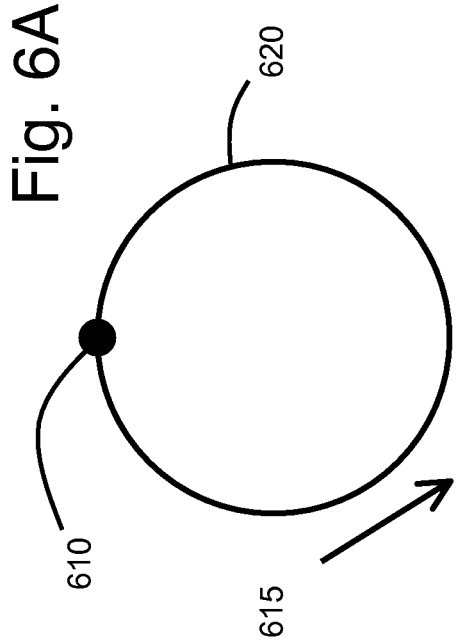

FIG. 6A illustrates a camera path in a world coordinate system. The camera begins at a starting point 610 and follows a path 620 in a counterclockwise direction as indicated by an arrow 625, returning to an ending point coincident with the starting point 610 in a fixed coordinate system, such as an arbitrarily selected world coordinate system.

FIG. 6B shows a camera path in a camera coordinate system. When a camera traverses the path 620 in the world coordinate system, errors may accumulate in a calculated camera path 635 so that a measured ending point 640 appears to be located away from the measured starting point 630 in the camera coordinate system, even though these points are identical in the world coordinate system. In one aspect, one or more cross links such as those described above with reference to FIG. 4 may be employed to mitigate accumulated errors in the calculated camera path 635.

Figure 7:
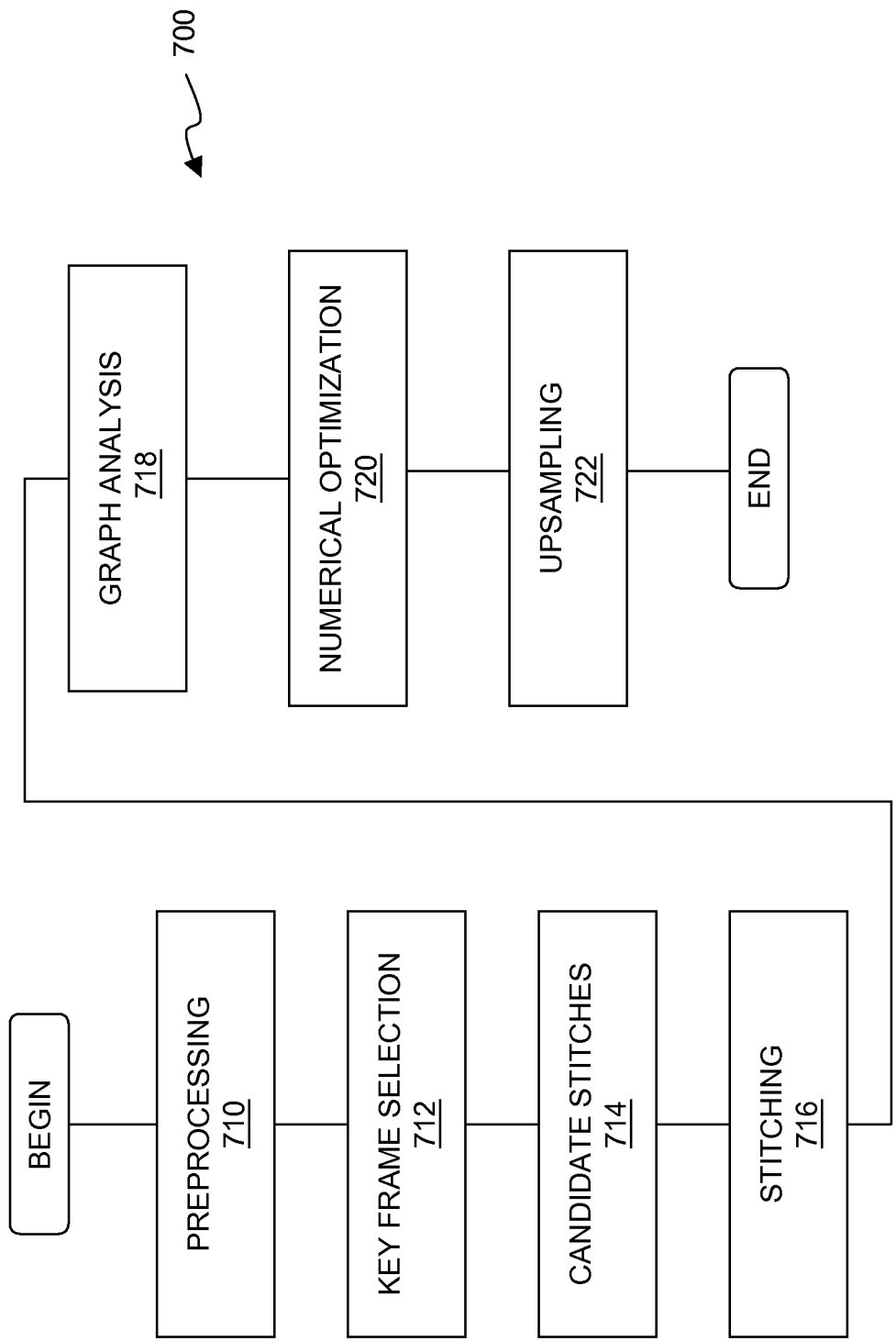
FIG. 7 is a flow chart of a three-dimensional reconstruction process including global path optimization for improved accuracy.

FIG. 7 is a flow chart of a three-dimensional reconstruction process including global path optimization for improved accuracy.

The process 700 may begin with preprocessing as shown in step 710. It will be understood that preprocessing as described herein presupposes the availability of a number of frames of image data from which a camera path and three-dimensional model can be reconstructed. The information for the three-dimensional reconstruction may be generated in numerous ways including coming from structured light projection, shading based three-dimensional reconstruction, or disparity data. Disparity data may be generated by a conventional image plus one or more other channels or side channels. The preprocessing may include determining the number of available frames, the amount of overlap between neighboring frames, identification and elimination of frames with blurred or badly distorted images, and any other suitable preprocessing steps. An estimate of the number of desired key frames may be initially determined during the preprocessing step.

As shown in step 712, key frames may be selected from among all of the frames of data acquired from a camera along a camera path. In general, computational costs can be reduced by storing certain data and performing certain calculations and processing steps exclusively with reference to key frames. These key frames may be related to one another in a manner that permits characterization of a complete camera path, typically through the registration of overlapping three-dimensional data in respective key frames. Various methods are known in the art for selecting a subset of frames of data as key frames, including techniques based on image overlap, camera path distance, the number of intervening non-key frames and so forth. Key frames may also or instead be selected based upon an amount of image overlap from the preceding key frame and/or a candidate for a following key frame (if available). Too little overlap may impair frame-to-frame registration. Too much overlap may produce excess key frames requiring additional processing. Key frames may be selected based on spatial displacement. Key frames may also be selected based on sequential displacement. This type of sequential displacement could mean for example that every tenth frame is selected as a key frame. In one aspect, key frames may be selected as data is acquired based on any number of suitable criteria. In another aspect, key frame pairs may be determined post hoc by examining all possible candidate key frames. All possible key frame pairs may be examined and candidates may be removed, for example, where there is insufficient overlap to form a stitch. Still more generally, any technique suitable for selecting a subset of frames in a data set may be usefully employed to select key frames for processing in order to reduce computational complexity.

Once key frames have been selected, additional processing may be performed. For example, full image data (e.g., full resolution center and side channel images) may be stored for each key frame, along with image signature data, point cloud centroid calculations, and any other measured or calculated data to support use of the key frames in a three-dimensional reconstruction process as described herein.

As shown in step 714, candidate stitches may be identified. In general, a stitch is a relationship between two separate three-dimensional measurements from two different camera poses. Once a stitch is established, a rotation and a translation may be determined for the path of a camera between the two poses. In a complementary fashion, the three-dimensional measurements from the poses may be combined into a portion of a three-dimensional model. Candidate stitches may be analyzed around each key frame, such as from the key frame to some or all of the frames of data between the key frame and neighboring key frames. In another aspect, a candidate stitch may be made to every other key frame, or in order to reduce computational complexity, every key frame within a spatial or sequential neighborhood around a key frame. Stitches may be based on the originally imaged frames. It may also be useful to deform or warp two-dimensional images during registration and other steps in a stitching process in order to improve accuracy and/or speed. Stitches may also or instead be based on other observed epipolar relationships in source data.

As shown in step 716, stitches may be selected for the complete camera path from the universe of candidate stitches. The selection of stitches may be made based upon, e.g., the lowest calculated error in resulting portions of the three-dimensional model. In general, each key frame may be stitched to one or more other key frames and each non-key frame may be stitched to at least one sequentially neighboring key frame.

As shown in step 718, a graph analysis may be performed using the key frames and the associated stitching to calculate a global path for the camera used to obtain a three-dimensional model. The graph analysis may consider each key frame as a node or vertex and each stitch as an edge between a pair of nodes. A key frame is selected as a starting point. A breadth- or depth-first search may be performed through the graph to identify stitches which may connect the current key frame to another key frame. Each key frame may be marked as the graph is processed. A check may be performed to see if all key frames have been reached within the graph. If all key frames have not been reached through traversing stitches in the graph analysis, the largest sub-graph is identified. This sub-graph may be examined to see if the entire three-dimensional image may be modeled.

It may be that certain sub-graphs are not required to complete the three-dimensional imaging. If the camera lingered over a particular region of a surface of an object, or if the camera looped on a region multiple times, the associated sub-graph(s) may not be needed. If a separate sub-graph is identified, which is needed to complete the three-dimensional imaging, an optional branch back to step 712 may be performed. For example, a set of key frames may have been selected which did not have sufficient stitching from one key frame to the next key frame. By choosing a different set of key frames, sufficient stitching may be obtained in order to obtain a complete graph of all needed aspects of the three-dimensional imaging. A key frame which is too sparse, meaning it has insufficient stitches to aid in building a graph, may indicate that a different set of key frames should be selected. Based on the graph analysis, a global path may be selected, and the graph may then be analyzed to optimize the path calculation.

As shown in step 720, a numerical optimization may be performed to reduce errors in the calculated camera path based upon available data for the complete camera path such as, for example, cross links that interrelate temporally distant measurements. In general, the objective of numerical optimization is to minimize a calculated error based upon an error function for the camera path and/or reconstructed three-dimensional model. A useful formulation of the error minimization problem for a global camera path is presented below.

In general, a set of related measurements in a path may be captured from three poses, A, B, and C, each related to one another and to a world coordinate system having an origin, O, by motion parameters of rotation and a translation. The relationship between a point, X, expressed in the world coordinate system as $X_O$ and the same point expressed in the A coordinate system, $X_A$ may be expressed as:

$$X_A = R_{OA} X_O + T_{OA} \quad [\text{Eq. 1}]$$

$R_{OA}$ is the rotation taking points from the world to the A coordinate system. $T_{OA}$ is the translation of the world coordinate system to the A coordinate system. It should be understood that symbols X and T may represent a vector, rather than a scalar, e.g. where X includes x, y, and z coordinate values. Further, it should be understood that symbol R may represent a matrix. The following equations may similarly represent the transformation between the world and the B and C coordinate systems respectively:

$$X_B = R_{OB} X_O + T_{OB} \quad [\text{Eq. 2}]$$

$$X_C = R_{OC} X_O + T_{OC} \quad [\text{Eq. 3}]$$

By rearranging, equations 1 and 2 may be represented as follows:

$$X_O = R_{OA}^{-1}(X_A - T_{OA}) = R_{OB}^{-1}(X_B - T_{OB}) \quad [\text{Eq. 4}]$$

The representation of a point in one camera's coordinate system may be related to the same point in another camera's coordinate system. For example, as in equations 1-3, coordinates of a point, X, may be transformed from the A coordinate system to the B coordinate system as follows:

$$X_B = R_{AB} X_A + T_{AB} \quad [\text{Eq. 5}]$$

The rotation $R_{AB}$ rotates points from the A to the B coordinate system and $T_{AB}$ translates the origin of the A coordinate system in the B coordinate system.

In optimization, the pose of every camera may be optimized based on measured transformations between poses. That is, a number of camera-to-world rotations and camera-to-world translations, $R_{On}$ and $T_{On}$ may be performed. In general, one of these may be defined as the identity rotation and zero translation, with the remaining values being optimized as described below.

The rotations and translations may be measured for many pairs of cameras. For the ith such measured frame-to-frame motion, let one of the cameras of the pair be camera A and the other be camera B. This may also be considered the ith stitch. Let $R_{AB}^i$ be the measured rotation taking points in the A system to the B system and $T_{AB}^i$ be the coordinates of the A position expressed in the B system, as in equation 5.

The rotations and translations for all cameras, $R_{On}$ and $T_{On}$ may be optimized. $R_{C,OA}^i$ and $R_{C,OB}^i$ may be defined to be the candidate rotations; $T_{C,OA}^i$ and $T_{C,OB}^i$ may be defined to be the candidate translations corresponding to the A and B camera of the ith stitch. Further, $R_{C,AB}^i = R_{C,OB}^i (R_{C,OA}^i)^{-1}$ may be defined as the candidate rotation from A to B, and $T_{C,AB}^i = T_{C,OB}^i - R_{C,AB}^i T_{C,OA}^i$, the candidate translation for the transformation from A to B.

Note that with sufficient stitches, the motion constraints may form an overdetermined system of motion constraint equations. Using these equations as a starting point, numerical optimization may be performed on the rotational and translational components of each camera based on the measured stitches.

In a decoupled optimization, the rotational and translational components may be independently optimized. Given a candidate set of camera rotations, $R_C^i$ the corresponding candidate camera-to-camera rotations, $R_{C,AB}^i$, may be computed that correspond to each of the measured camera-to-camera rotations, $R_{AB}^i$. Thus the corresponding residual rotations are given by $R_{residual,AB}^i = R_{C,AB}^i (R_{AB}^i)^{-1}$. A scalar-valued rotational cost function, $e_r$, may be computed that depends on the candidate camera rotations $$e_r(R_{C,On}) = \sum_{i=1}^{\#stitches} r_r^{iT} r_r^i, \text{ where } r_r^i = \log_{SO(3)} R_{residual,AB}^i, \quad [\text{Eq. 6}]$$

In equation 6, $\log_{SO(3)}(R)$ returns the axis-angle vector, v, that corresponds to the rotation R. In other words, $\log_{SO(3)}(R)$ returns the vector, v, that has a cross-product matrix, $[v]_x$, that is the matrix logarithm of R.

Next, a similar scalar-valued cost function may be computed for translation that depends on the candidate rotations and translations.

$$e_t(R_{C,On}, T_{C,On}) = \sum_{i=1}^{\#stitches} r_t^{iT} r_t^i, \text{ where } r_t^i = T_{C,AB}^i - T_{AB}^i \quad [\text{Eq. 7}]$$

Equation 6 may be minimized as a nonlinear optimization; equation 7 may be minimized as a linear optimization.

In one conventional, decoupled approach to solving these simultaneous systems of equations, the rotational error function may be converted into a quaternion expression in order to translate the numerical problem into a linear system of equations for solution. While this approach may increase computational efficiency, it offers an incomplete optimization solution.

The decoupled approach described above does not provide a truly optimal one, in a maximum-likelihood sense, as it cannot use information from the translation portion of the stitches in determining rotation. In order to achieve a coupled optimization a weighting may be used to balance the contributions of rotational and translational components to a combined cost function:

$$e_c(R_{C,On}, T_{C,On}) = \sum_{i=1}^{\#stitches} \left( \begin{bmatrix} r_t^i \\ r_r^i \end{bmatrix}^T W_c^i \begin{bmatrix} r_t^i \\ r_r^i \end{bmatrix} \right) \quad [\text{Eq. 8}]$$

Multiple approaches may be used to optimize this cost function, but in one embodiment the weights may be expressed as matrices. Different stitches may receive different weightings based upon a number of factors including the number of points in the stitch (e.g., the shared content), the quality of a particular three-dimensional measurement, and/or any other factors impacting the known reliability of a stitch. In one approach, the weight matrices may also account for anisotropic error in the individual points collected, such as due to acquisition of depth information from disparity measurements, which results in measurement precision that varies with distance from the camera.

In some cases, equation 8 may be reformulated so that the rotation and translation weights are decoupled for each stitch (i.e., $W_c^i$ is a block diagonal). In particular, this may occur in the case where the motion stitches are recovered from three-dimensional point correspondences with isotropic point error. In that case, for a given stitch i, between camera A and camera B, the optimal solution may bring the point cloud as seen from camera A into correspondence with that seen from camera B. If $\overline{X}_A^i$ and $\overline{X}_B^i$ are the positions of the center of the point cloud in the A and B systems respectively, then $r_t^i$ may be replaced in equation 8 with the residual displacement between the point-cloud centers based on the candidate camera pose as follows:

$$r_{t,ctr}^i = \overline{X}_B^i - (R_{C,AB}^i \overline{X}_A^i + T_{C,AB}^i) \quad [\text{Eq. 9}]$$

Equation 8 may then be reformulated as:

$$e_c(R_{C,On}, T_{C,On}) = \sum_{i=1}^{\#stitches} \left( r_{t,ctr}^{iT} W_t^i r_{t,ctr}^i + r_r^{iT} W_r^i r_r^i \right) \quad [\text{Eq. 10}]$$

This coupled optimization problem may still be considered as being non-linear. It should be understood that other optimizations are also possible that would fall within the scope of this disclosure.

In general, by minimizing equation 8, both rotational errors and translational errors may be minimized simultaneously. The weight matrices can be chosen, for example, according to "First Order Error Propagation of the Procrustes Method for 3D Attitude Estimation" by Leo Dorst, IEEE Transactions on Pattern Analysis and Machine Intelligence, Vol. 27, No. 2, February 2005, pp. 221-9 which is incorporated in its entirety by reference. Once a more consistent set of motion parameters has been generated the three-dimensional model may be updated.

In one aspect, the residual error may be employed as a calibration metric. When total error or some portion of error has been minimized, the residual error may be evaluated. If a minimized error falls beyond a certain threshold then calibration for the camera and associated hardware may be recommended, based upon an inference that the inability to produce better quality results is due to a miscalibration or other malfunction of the camera system. The threshold value may be empirically determined based on the specific camera hardware equipment or it may be learned experientially over time for a given system. When a system is new or has been freshly aligned, expected minimized error values may be obtained. When minimized error values deviate from these expected values, a calibration state evaluation flag may be set, or other alert or message generated, indicating that the tool should be calibrated.

As shown in step 722, upsampling may be performed to augment a three-dimensional model with data from non-key frames. For example, non-key frames may be registered to nearby key frames to create small, local reconstruction patches including the full image detail available from non-key frames. In this manner, path optimization may be performed on a key-frame-based data set, thus reducing the data requiring processing, while retaining additional data points from non-key frames for use in the final three-dimensional model.

It will be appreciated that any of the above system and/or methods may be realized in hardware, software, or any combination of these suitable for the data acquisition and modeling technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. Thus in one aspect there is disclosed herein a computer program product comprising computer executable code that, when executing on one or more computing devices, performs any and/or all of the steps described above. At the same time, processing may be distributed across devices such as a camera and/or computer and/or fabrication facility and/or dental laboratory and/or server in a number of ways or all of the functionality may be integrated into a dedicated, standalone device. All such permutations and combinations are intended to fall within the scope of the present disclosure.

What is claimed is:

1. A method of three-dimensional reconstruction comprising:
    acquiring a plurality of frames of image data of a surface of an object, each one of the plurality of frames of image data captured from a camera position along a camera path and each one of the plurality of frames of image data providing an independent three-dimensional data set including a conventional image of the object from the camera position and disparity data stored in the frame for a three-dimensional reconstruction of the surface of the object as viewed from the camera position;
    selecting a subset of the plurality of frames of image data to provide a plurality of key frames, each one of the plurality of key frames related to at least one other one of the plurality of key frames by a portion of the camera path including a rotation and a translation determined based upon one or more common points in the three-dimensional reconstruction of the surface of the object in each of the respective key frames, wherein the plurality of key frames provide coverage for a substantial portion of the surface of the object and wherein the remaining ones of the plurality of frames of image data are non-key frames;

estimating a camera motion between two adjacent key frames wherein the estimating is based on the rotation and the translation;

optimizing the estimation of the camera motion between the two adjacent key frames by creating consistency among motion parameters using an overdetermined system of motion constraint equations, wherein the motion parameters are comprised of information on the rotation and the translation;

providing a three-dimensional model of the object based upon the camera path for the plurality of key frames;

determining a second rotation and a second translation from one of the key frames to at least one of the non-key frames sequentially positioned between the one of the key frames and a sequentially adjacent one of the key frames;

obtaining three-dimensional reconstruction information of the surface of the object from the camera position of the at least one of the non-key frames to provide upsampled three-dimensional data; and adding the upsampled three-dimensional data to the three-dimensional model based upon the second rotation and the second translation.

2. The method according to claim 1 further comprising optimizing the camera motion between two adjacent non-key frames by creating consistency among motion parameters using an overdetermined system of motion constraint equations.

3. The method according to claim 2 further comprising updating the three-dimensional reconstruction based on the created consistency among the motion parameters.

4. The method according to claim 1 wherein the data for a three-dimensional reconstruction of the surface of the object was obtained from at least one other channel image to provide disparity data.

5. The method according to claim 1 wherein providing a three-dimensional model further comprises generating a three-dimensional model of the object using the camera path and the three-dimensional reconstruction for each of the key frames.

6. The method according to claim 1 further comprising obtaining three-dimensional reconstruction information of the surface of the object from the camera position for all of the non-key frames between two adjacent key frames.

7. The method according to claim 1 wherein the selecting of the subset of the plurality of frames is based on a quality metric of the three-dimensional reconstruction.

8. The method according to claim 1 wherein the selecting of the subset of the plurality of frames is determined using graph analysis to ensure that all of the key frames are utilized in the three-dimensional reconstruction.

9. The method of claim 1 wherein selecting the subset of the plurality of frames includes selecting a number of the frames that permits characterization of a complete camera path through registration of overlapping three-dimensional data.

10. The method of claim 1 wherein selecting the subset of the plurality of frames includes selecting a number of the frames based on a camera path distance.

11. The method of claim 1 wherein selecting the subset of the plurality of frames includes selecting a number of the frames based on a number of intervening non-key frames.

12. The method of claim 1 wherein selecting the subset of the plurality of frames includes selecting one of the key frames based on an amount of image overlap with an image in an adjacent key frame.

13. The method of claim 1 wherein selecting the subset of the plurality of frames includes selecting one of the key frames based on a spatial displacement from a preceding one of the key frames.

14. The method of claim 1 wherein selecting the subset of the plurality of frames includes selecting one of the key frames based on a sequential displacement from a preceding one of the key frames.

15. The method of claim 1 wherein selecting the subset of the plurality of frames includes selecting one of the frames and evaluating the one of the frames for suitability as a key frame.

16. The method of claim 1 further comprising identifying two of the plurality of key frames that represent a candidate for an accumulated error in the camera path relative to one another.

17. The method of claim 16 further comprising displaying the three-dimensional model along with a graphical annotation that illustrates a recommended scan path to reduce the accumulated error.

18. The method of claim 17 further comprising acquiring one or more frames of image data along the recommended scan path to reduce the accumulated error.

19. The method of claim 1 further comprising minimizing an error function for a plurality of camera positions along the camera path, the error function including a system of equations for translational components of an error and for rotational components of the error, wherein the error function couples the translational components and the rotational components using a weighting matrix, thereby providing an optimized camera path.

20. The method of claim 19 wherein the system of equations is a non-linear system of equations.

21. The method of claim 20 wherein the translational component of the error forms a system of linear equations.

* * * * *